United States Patent
Limousin

(10) Patent No.: US 9,421,374 B2
(45) Date of Patent: *Aug. 23, 2016

(54) ACTIVE IMPLANTABLE MEDICAL DEVICE FOR VAGAL STIMULATION WITH OPTIMIZATION OF VENTRICULAR FILLING

(71) Applicant: SORIN CRM SAS, Clamart (FR)

(72) Inventor: Marcel Limousin, Paris (FR)

(73) Assignee: SORIN CRM SAS, Clamart (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/671,380

(22) Filed: Mar. 27, 2015

(65) Prior Publication Data

US 2015/0202445 A1 Jul. 23, 2015

Related U.S. Application Data

(63) Continuation of application No. 13/082,278, filed on Apr. 7, 2011, now Pat. No. 8,996,105.

(30) Foreign Application Priority Data

Apr. 8, 2010 (FR) ..................................... 10 52649

(51) Int. Cl.
*A61N 1/36* (2006.01)

(52) U.S. Cl.
CPC ....... *A61N 1/36117* (2013.01); *A61N 1/36114* (2013.01); *A61N 1/36139* (2013.01)

(58) Field of Classification Search
CPC ..................... A61N 1/36114; A61N 1/36139
See application file for complete search history.

(56) References Cited

U.S. PATENT DOCUMENTS

| | | |
|---|---|---|
| 5,304,208 A | 4/1994 | Inguaggiato et al. |
| 5,496,531 A | 3/1996 | Davis et al. |
| 5,916,239 A | 6/1999 | Geddes et al. |
| 6,604,002 B2 | 8/2003 | Molin |
| 6,725,091 B2 | 4/2004 | Dal Molin |
| 7,123,961 B1 | 10/2006 | Kroll et al. |
| 2004/0176695 A1 | 9/2004 | Poezevara |

(Continued)

FOREIGN PATENT DOCUMENTS

| | | |
|---|---|---|
| EP | 0 515 319 A2 | 11/1992 |
| EP | 0 655 260 A2 | 5/1995 |

(Continued)

OTHER PUBLICATIONS

Preliminary Search Report for French Patent Application No. 1052649, dated Aug. 3, 2010, 2 pages.

*Primary Examiner* — William Levicky
(74) *Attorney, Agent, or Firm* — Foley & Lardner LLP

(57) ABSTRACT

An active implantable medical device for vagal stimulation with optimization of ventricular filling is disclosed. The device delivers stimulation pulses to the vagal nerve of the patient with an adjustable energy level. The device includes a hemodynamic sensor for measuring hemodynamic parameters of the patient's cardiac cycles and delivering a timing parameter representative of the ventricular filling time. The energy level of the vagal stimulation pulses is adjusted dynamically and repeatedly over several cardiac cycles. The energy level is varied during successive cardiac correlative changes in the filling time (FT1, FT2) are assessed, and the energy level is set to a level that maximizes the ventricular filling time.

18 Claims, 3 Drawing Sheets

(56) References Cited

U.S. PATENT DOCUMENTS

| | | |
|---|---|---|
| 2006/0100668 A1 | 5/2006 | Ben-David et al. |
| 2006/0122675 A1* | 6/2006 | Libbus .................. A61N 1/0551 607/116 |
| 2006/0264764 A1 | 11/2006 | Ortiz-Burgos |
| 2007/0299476 A1* | 12/2007 | Park ................... A61N 1/36114 607/9 |
| 2008/0119898 A1 | 5/2008 | Ben-David et al. |
| 2008/0125827 A1 | 5/2008 | Ben-David et al. |
| 2008/0281368 A1 | 11/2008 | Bulkes et al. |
| 2009/0209875 A1* | 8/2009 | Giorgis .............. A61B 5/02028 600/512 |
| 2010/0198293 A1 | 8/2010 | Kaiser et al. |

FOREIGN PATENT DOCUMENTS

| | | |
|---|---|---|
| EP | 1 116 497 A1 | 7/2001 |
| EP | 1 138 346 A1 | 10/2001 |
| EP | 1 433 496 | 6/2004 |
| EP | 2 092 885 A1 | 8/2009 |

* cited by examiner

ACTIVE IMPLANTABLE MEDICAL DEVICE FOR VAGAL STIMULATION WITH OPTIMIZATION OF VENTRICULAR FILLING

CROSS-REFERENCE TO RELATED PATENT APPLICATIONS

This application is a continuation of U.S. application Ser. No. 13/082,278, filed Apr. 7, 2011, which claims the benefit of and priority to French Application No. 10/52649, filed Apr. 8, 2010, both of which are hereby incorporated by reference herein in their entireties.

TECHNICAL FIELD

The present invention relates to "active implantable medical devices" as defined by the 20 Jun. 1990 Directive 90/385/EEC of the Council of the European Communities, and more particularly to implantable medical devices for vagal stimulation, namely stimulating the vagus nerve of a patient for, among other indications, controlling a patient's blood pressure by acting on the sympathetic nerve system.

BACKGROUND

Active implantable medical devices for vagal stimulation generally include a generator implanted in a patient and a lead that is electrically connected to the implanted generator. The lead carries at its distal end one or more electrodes that are placed in contact with the vagus nerve of the patient at the carotid artery to deliver electrical stimulation pulses with a controlled and adjustable energy level. Vagus nerve stimulation by electrical pulses provides control of the blood pressure of the patient, thus it may be used as a treatment choice for hypertension when the treatment of hypertension by medication is deemed ineffective or not suitable.

One type of known vagal stimulation device is described in U.S. Pat. No. 7,123,961 B1. The generator is equipped with an energy management system for stimulating the vagus nerve of a patient and managing and controlling various parameters such as the patient's myocardial contractility (i.e., inotropy), heart rate, and/or atrioventricular conduction (i.e., dromotropy). These parameters are controlled according to the results of an analysis on the components of the patient's cardiac rhythm, including the heart rate, the PR interval, and the QRS complex duration.

U.S. Patent Publication Nos. 2008/0125827 A1, 2008/0119898 A1 and 2006/0111668 A1 describe similar vagal stimulation devices.

The starting point for the present invention stems from clinical observations that hypertension that cannot be adequately treated by medication is prevalent among patients with heart failure, especially those suffering from "diastolic heart failure". In these patients, the function of the left heart is preserved, meaning that the contractility of the left ventricle is not affected, and the heart failure in such patients is linked to a poor filling capacity. For this reason, diastolic heart failure is also referred to as heart failure "with preserved systolic function". The pathology of diastolic heart failure is characterized by an abnormally reduced filling phase during the diastole because these patients have left ventricular hypertrophy that provides inadequate diastolic filling.

The presence of hypertension is an additional barrier to optimal diastolic filling. However, if hypertension is treated by vagal stimulation, its effectiveness is constrained to be dependent on the stimulation energy level; the higher the voltage (energy level) delivered by the device, the larger the reduction in the blood pressure. However, strong energy stimulation pulses significantly limit the lifetime of the implantable medical device due to excessive power consumption.

SUMMARY

It is, therefore, an objective of the present invention to provide an implantable medical device for vagal stimulation suited for patients who have heart failure with preserved systolic function (i.e., patients having a diastolic heart failure) and uncontrolled hypertension.

In one embodiment, the present invention is directed to a medical device that indirectly monitors a patient's blood pressure by measuring the time of left ventricular filling from parameters obtained from a sensor measuring hemodynamic parameters of the patient's cardiac cycles.

The left ventricular or diastolic filling time is the time interval between the closure of the aortic valve and the closure of the mitral valve. Because patients with heart failure with preserved systolic function exhibit a significant reduction of the diastolic filling time, the vagal stimulation therapy may be controlled based on the left ventricular or diastolic filling time.

In one embodiment, the sensor for measuring hemodynamic parameters of a patient's cardiac cycle is an endocardial acceleration (EA) sensor. An EA sensor provides not only the indirect measurement of dP/dt, time rate changes of the blood pressure in the left ventricle, but also various characteristic moments of the systolic and diastolic phases, generating appropriate markers for those characteristic instances.

In addition, the use of an EA sensor is advantageous in assessing the myocardial contractility of the patient from the dP/dt pressure variations. The vagal stimulation energy level may be adjusted to optimize the filing time while monitoring the myocardial contractility to avoid an undesired effect referred to as a "negative inotropic effect." A negative inotropic effect is characterized by a reduced contractility of the left ventricle due to the vagal stimulation.

In one embodiment, the present invention provides an active implantable medical device of a type disclosed by U.S. Patent Publication No. 2008/0125827 A1 cited above, comprising: means for stimulating the vagus nerve of a patient by repeatedly delivering to the vagus nerve, during successive cardiac cycles, stimulation pulses having an adjusted vagal stimulation energy level; a sensor for measuring hemodynamic parameters of cardiac cycles and delivering a temporal parameter representative of the ventricular filling time; means for adjusting the vagal stimulation energy level, dynamically repeatedly operating over several cardiac cycles.

In one embodiment, the means for varying the vagal energy stimulation level varies the stimulation energy level during successive cardiac cycles and assesses correlative variations of the filling time. The device further comprises means for establishing the stimulation energy level at a level that maximizes said ventricular filling time.

In a preferred embodiment, the sensor for measuring hemodynamic parameters of the patient's cardiac cycles is an EA sensor and the means for adjusting the vagal stimulation energy comprises: means for isolating in a signal delivered by the EA sensor at least one component corresponding to a peak of endocardial acceleration ("PEA"); means for operating a morphological analysis of the at least one component; and means for deriving a parameter representative of the temporal ventricular filling time from the results of said morphological analysis.

Preferably, the means for adjusting the vagal stimulation energy level further includes: means for comparing the measured ventricular filling time to a predetermined threshold; and means for limiting said adjusted level to the current stimulation energy level when the measured ventricular filling time reaches or exceeds said threshold.

In another preferred embodiment, the sensor for measuring hemodynamic parameters of the patient's cardiac cycles delivers a hemodynamic parameter representative of the left ventricular contractility, and the means for adjusting the vagal stimulation energy level also include: means for evaluating the changes of the hemodynamic parameter during successive cardiac cycles; and means for limiting said adjusted vagal stimulation energy level to the current stimulation energy level in case of an increase of the hemodynamic parameter in response to an increased vagal stimulation energy level.

In one particular embodiment, in case when an EA sensor is used, the means for measuring hemodynamic parameters includes: means for isolating in a signal delivered by the EA sensor at least one component corresponding to a peak of endocardial acceleration; and means for deriving from said at least one component a hemodynamic index.

In one embodiment, the medical device comprises means for activating the means for adjusting the vagal stimulation energy level at predetermined regular intervals, and/or means for detecting predetermined changes of the patient's state and activating the means for adjusting the vagal stimulation energy level on detection of at least one state change of the predetermined changes of the patient's state, the predetermined state changes being selected from among the group consisting of a presence or absence of an arrhythmia; and a transition between phases of rest, effort, sleep, and any other state of the patient identifiable by the sensor for measuring hemodynamic parameters of the patient's cardiac cycles.

The sensor for measuring hemodynamic parameters of the patient's cardiac cycles is preferably a sensor selected from among the group consisting of: an endocardial or epicardial acceleration sensor, a cardiac wall motion sensor, an intracardiac pressure sensor; an intracardiac bioimpedance sensor, an optical oxygen saturation sensor; and an ultrasound sensor for measuring changes in volume.

BRIEF DESCRIPTION OF THE DRAWINGS

Further features, characteristics and advantages of the present invention will become apparent to a person of ordinary skill in the art from the following detailed description of exemplary and preferred embodiments of the present invention, made with reference to the drawings annexed, in which like reference characters refer to like elements, and in which.

DETAILED DESCRIPTION

An example of exemplary and preferred embodiments of a device according to the present invention will now be described.

As regards its software aspects, the present invention may be implemented by an appropriate programming of controlling software of an implantable medical device of known types, for example, a cardiac pacemaker or a defibrillator/cardioverter, including means for collecting signals provided by endocardial leads and/or one or more implanted sensors. These devices include programmable microcontroller and/or microprocessor circuitry to receive, format, and process electrical signals collected (detected) from the implanted electrodes and deliver stimulation pulses to selected one or more electrodes of the implanted electrodes. It is possible to transmit by telemetry software and store it in a memory of the implantable medical devices and execute the stored software to implement functions of the present invention. The adaptation of these implantable medical devices to implement the functions and features of the present invention is believed to be within the abilities of a person of ordinary skill in the art, and therefore will not be described in detail. The present invention may particularly be applied to implantable medical devices such as those of the Reply or Paradym device families produced and marketed by Sorin CRM, Clamart France, formerly known as ELA Medical, Montrouge, France.

Figure 1:
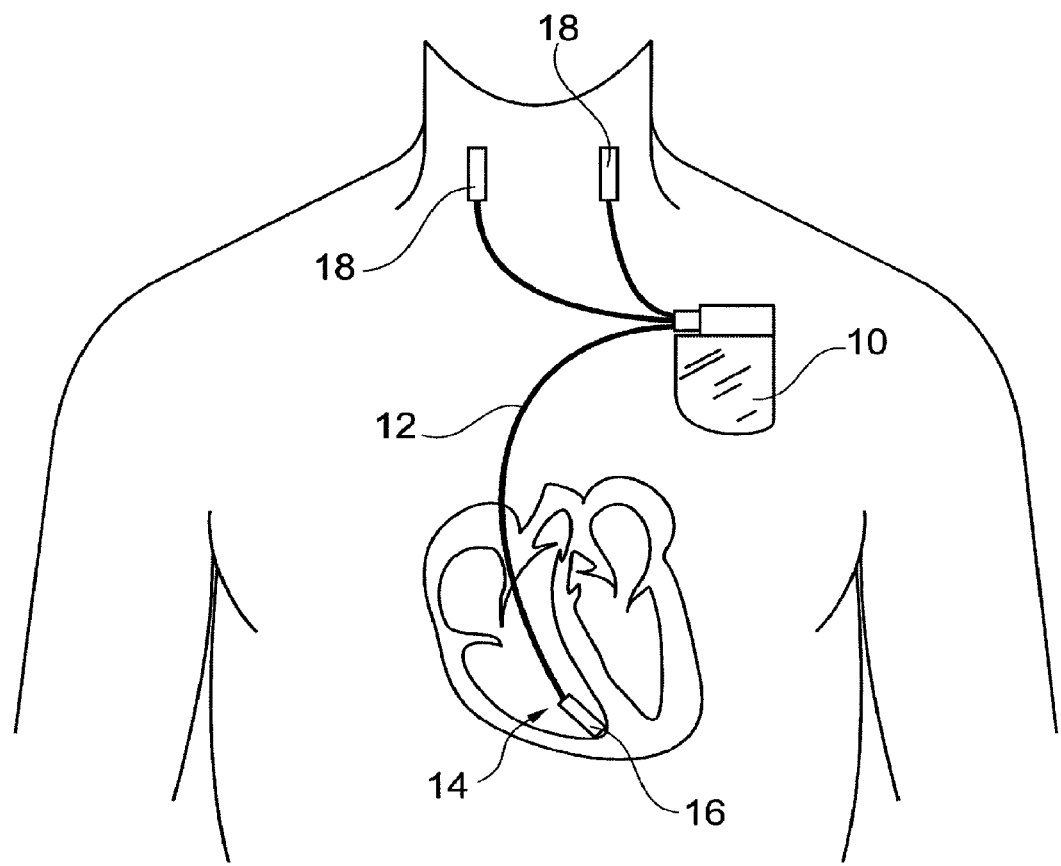
FIG. 1 is a schematic view of a vagal stimulation medical device implanted in a patient with an endocardial lead and electrodes for stimulating the patient's vagus nerve.

With reference to FIG. 1, a generator 10 is connected to a lead 12 having at its distal end 14 a sensor 16 for measuring hemodynamic parameters of cardiac cycles of the patient. The lead 12 may include various electrodes for collecting signals representative of the depolarization of the patient's heart and/or cardiac pacing. These electrodes for collecting depolarization signals for cardiac pacing are not directly associated with the present technique for providing vagal stimulation pulses.

The sensor 16 for measuring the hemodynamic parameters of the patient's cardiac cycles measures variations in the volume of the left ventricle, and/or the movement of the muscle fibers of the left ventricle, during different phases of the cardiac cycle. These different phases include: pre-ejection, isovolumetric contraction, systolic ejection, isovolumetric relaxation, and filling of the ventricular cavity.

The present invention is particularly directed to the duration of the left ventricular filling or Diastolic Filling Time (DFT) that is a time interval measured between the instant of closure of the aortic valve and the instant of closure of the mitral valve.

The characteristic instants marking these various phases of a cardiac cycle may be determined using a technique such as the one described in EP 2092885 A1 and its counterpart U.S. Patent Publication No. 2009/0209875 (both assigned to Sorin CRM S.A.S., previously known as ELA Medical). These patent applications describe a technique for conducting a morphological analysis of an EA signal delivered by an accelerometer in contact with a heart muscle, including a sensor integrated to an endocardial lead. Data provided by such an EA sensor reflect very precisely and essentially in real time the phenomena contributing to the mechanical functioning of the patient's heart and provides, after filtering and analysis, temporal markers of the diastole as well as other indices of the hemodynamic performance of the myocardium. The collected temporal markers are correlated with the instants of opening and closing of the aortic, mitral, pulmonary and/or tricuspid valves, and the filling time is measured from the time between the closure of the aortic valve and the closure of the mitral valve. According to one embodiment, these parameters are determined in real-time or nearly real-time, beat to beat to estimate the instantaneous hemodynamic performance of the patient's heart and efficiently adapt the therapy applied to the patient.

In general, sensors for measuring hemodynamic parameters of cardiac cycles, also referred to as hemodynamic sensors, estimate changes in the myocardial contractility, correlated with increases in blood pressure. Hemodynamic sensors differ from activity sensors (e.g., acceleration sensors) and metabolic sensors (e.g., minute ventilation sensors) because activity sensors are intended to measure the presence or absence of the patient's physical activity level such as exercise, and metabolic sensors are intended to quantify the patient's metabolic needs, for example, to adapt the pacing heart rate based on the patient's detected level of physiological activity. The hemodynamic sensor may notably provide an indication of the patient's hemodynamic tolerance in relation to certain events, in particular, as discussed below, the tolerance to changes in the vagal stimulation parameters.

In some examples described herein, the sensor for measuring the hemodynamic parameters of cardiac cycles is an endocardial acceleration sensor (EA) sensor. These exemplary embodiments are, however, in no way limiting and the present invention can be implemented with other types of sensors for measuring hemodynamic parameters of cardiac cycles such as, but not limited to: an epicardial (not endocardial) acceleration sensor, a sensor for myocardium wall motion, an intracardiac systolic pressure sensor that determines the pressure difference between the systolic blood pressure and the diastolic blood pressure, an intracardiac bioimpedance sensor, an optical oxygen saturation sensor, an ultrasound sensor for measuring volume change.

For various descriptions of such sensors, one skilled in the art is referred to the following documents:

Endocardial acceleration type sensors are described in: 1) EP 0515319 A2 and its counterpart U.S. Pat. No. 5,304,208 (both assigned to Sorin Biomedica Cardio SpA), which describe a method to collect an EA signal using an endocardial lead provided with a distal stimulation electrode located at the apex of the ventricle and incorporating a micro-accelerometer that measures the endocardial acceleration, and 2) EP 0655260 A2 and its counterpart U.S. Pat. No. 5,496,351 (both assigned to Sorin Biomedica Cardio SpA), which describe a method for processing the measured EA signal to derive a value representative of the peaks of endocardial acceleration corresponding to the two major noises recognizable in each cardiac cycle of a healthy heart;

A transvalvular bioimpedance sensor (measuring between the atrium and the ventricle located on the same side of the heart) is described in: EP 1116497 A1 and its counterpart U.S. Pat. No. 6,604,002 (both assigned to Sorin CRM S.A.S., previously known as ELA Medical), which describe dynamic measurement of bioimpedance (BioZ) to assess the diastolic and systolic volumes and hence obtain an indication of the cardiac output and the ejection fraction;

A transeptal bioimpedance sensor (measuring between a site located on one side of the heart and a site located on the other side) is described in: EP 1138346 A1 and its counterpart U.S. Pat. No. 6,725,091 (both assigned to Sorin CRM S.A.S., previously known as ELA Medical), which describe another method for bioimpedance measuring and delivery of a representative value of the ejection fraction.

Endocardial acceleration signals collected by an EA sensor during a cardiac cycle form two major components that correspond to the two major heart sounds (S1 and S2 sounds of the phonocardiogram). Each of the collected EA signals contains the first component of endocardial acceleration ("EA1") and the second component of endocardial acceleration ("EA2") in each cardiac cycle. The first component of endocardial acceleration ("EA1") has amplitude variations that are closely linked to changes in pressure in the ventricle. The maximum peak-to-peak amplitude of the EA1 component, ("PEA1") is specifically correlated to the positive maximum of the pressure variation dP/dt in the left ventricle, therefore PEA1 may be used as a parameter representative of the myocardial contractility that relates to the level of activity of the sympathetic system. The second component of endocardial acceleration ("EA2") occurs during the phase of isovolumetric ventricular relaxation. The EA2 component is mainly produced by a sudden deceleration of the blood mass in the aorta after the aortic and pulmonary valve closure, therefore the EA2 component may be used as a parameter representative of the peripheral blood pressure at the beginning of the diastole phase.

The EA signals may contain one or two other components, e.g., EA3 and EA4, each of which respectively corresponds to the S3 and S4 sounds of the phonocardiogram.

In addition to the sensor 16 for measuring hemodynamic parameters of cardiac cycles, the generator 10 is also connected to electrodes 18 for vagus nerve stimulation, preferably in the form of bilateral electrodes placed at the carotid artery. The bilateral electrode configuration controls the patient's cardiac pressure.

Stimulation of the vagal system of a patient reduces the blood pressure in hypertensive patients. Essentially, the present invention enhances the control of vagal stimulation and optimizes the timing of the left ventricular filling (i.e., the filling time or "FT" parameter).

It is assumed that the optimum of this left ventricular filling time is achieved for FT>40% (the filling time is usually expressed as a relative percentage of the full duration of an entire cardiac cycle (e.g., RR duration). This value is called "target value".

A first embodiment of the present technique is illustrated with reference to FIG. 2. In this embodiment, a filling time is measured (step 24), giving a value FT2 that is compared (step 26) to the previous value FT1. If FT2>FT1 at test 26, that is to say, if the vagal stimulation led to an increase in the filling time, the value FT2 is compared to the target value S (step 28). Typically S=40% of the duration of a full cardiac cycle. If the filling time did not reach target S, the energy of vagal stimulation is increased by one step, and FT2 becomes the current value FT1 of the filling time (step 30). The filling time is measured with this new energy value of vagal stimulation (back at step 24) and compared to the previous value (step 26), and the process repeats. If the target value has been reached or if the FT value no longer grows, it is considered that the filling of the ventricle is satisfactory, and it is not necessary to further increase the vagal stimulation energy. A further increase in the energy level for the vagal stimulation not only reduces the usable battery life of the generator, but also poses a risk of introducing a negative effect of decreasing the ventricular contractility. The energy level of the vagal stimulation is maintained at the current level, and the iterative process terminates because this current energy level provides the optimal filling time (i.e., target value S).

If the test of step 26 did not reveal any increase in the filling time in response to an increase to the vagal stimulation energy level, it is considered that the optimum has been exceeded. The vagal stimulation energy level is then reduced by one step (step 32) to return to its previous value or, if the test was in response to a stimulation with minimum energy (step 22), the vagal stimulation is stopped. In cases where the vagal stimulation induces a decrease in the filling time instead of an increase) in the filling time, the vagal stimulation is immediately stopped because the vagal stimulation deteriorates the clinical status of the patient.

Once the optimal value is reached, the iterative method of adjustment of the energy level of stimulation is stopped, and the stimulation energy is stabilized at the reached final value. This situation is maintained until a change of the patient's condition is detected (step 34) or at the end of a predetermined delay (step 36), for example, a timeout period of six hours. The timer continues to count (step 38) the elapsed time or count the number of cardiac cycles since the last adjustment to the vagal stimulation energy.

On detection of a change of the patient's state or at the end of the timeout, the iteration process described above is restarted. The change of the patient's state is preferably detected by conventional sensors, for example, an acceleration sensor (G sensor) integrated to the generator 10, a minute ventilation sensor (MV sensor), or the endocardial acceleration sensor. Each of these sensors detects the change of the patient's state by analyzing the collected signals, such as patient's effort, prolonged rest, sleep, arrhythmias.

Another embodiment of the present technique is illustrated with reference to FIG. 3. It is noted that the first embodiment illustrated in FIG. 2 tests only the filling time. In contrast, the second embodiment illustrated in the flow chart of FIG. 3 seeks not only to acquire a filling time FT as long as possible, but it also tests changes in myocardial contractility resulting from the variation of the vagal stimulation energy level. Indeed, a decrease in left ventricular contractility resulting from vagus nerve stimulation can sometimes be seen (negative inotropic effect), and it is important not to compromise this parameter in the adjustment of the vagal stimulation energy level.

This second embodiment exploits an EA sensor and obtains temporal markers that identify characteristic instants of the cardiac cycle to calculate the filling time. In addition, the EA sensor also obtains a non-temporal parameter representative of the myocardial contractility. This parameter is typically obtained by measuring the maximum peak to peak of the EA signal collected from the sensor 16.

Figure 2:
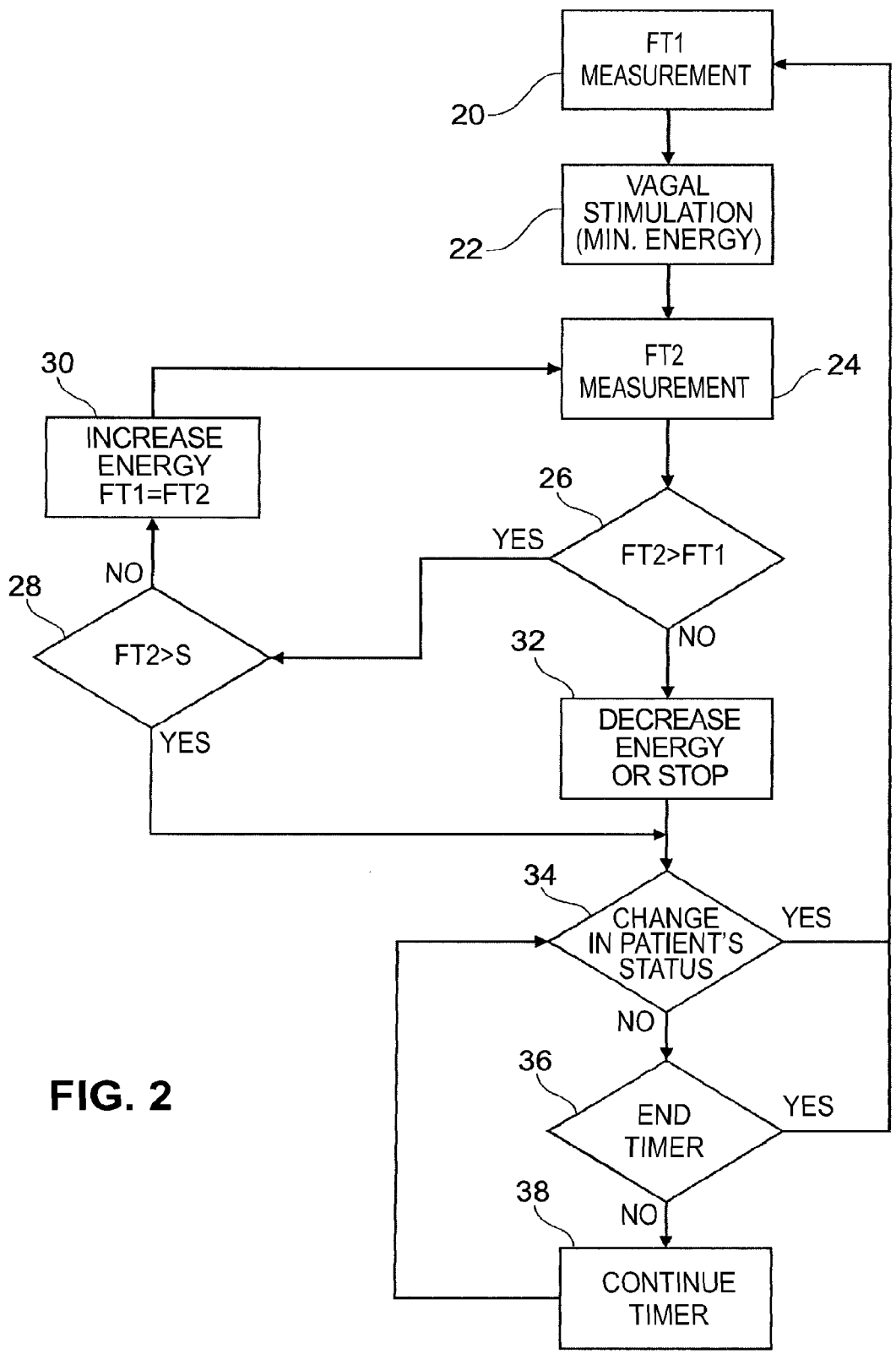
FIG. 2 is a flowchart illustrating a method for adjusting a vagal stimulation energy level, according to a first embodiment of the present invention.
Figure 3:
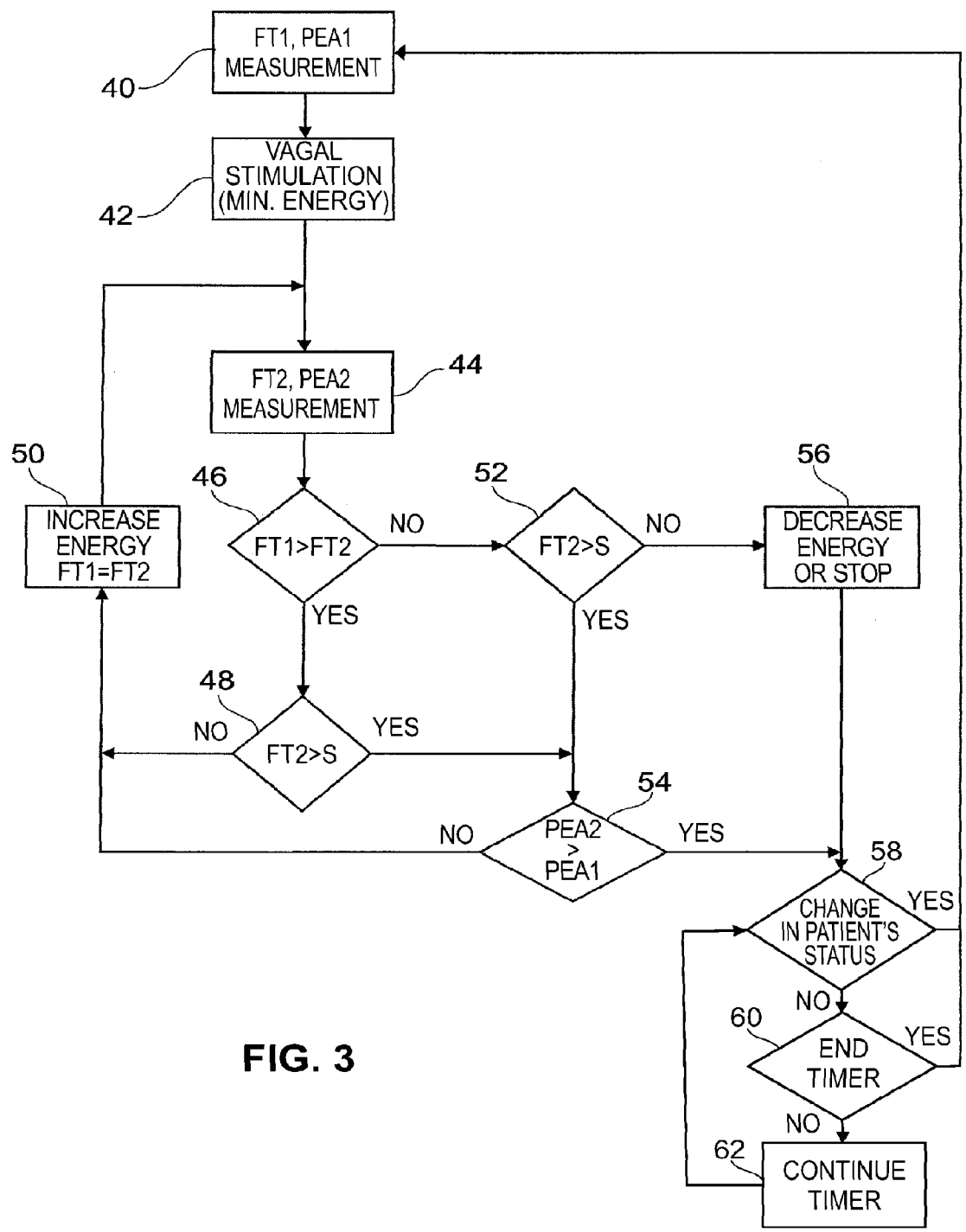
FIG. 3 is a flow chart illustrating a method for adjusting a vagal stimulation energy level, according to a second embodiment of the present invention.

Steps 40, 42 and 44 of FIG. 3 are similar to steps 20, 22 and 24 of FIG. 2 except that steps 40 and 44 not only measure the filling times FT1 and FT2 before and after a change of the vagal stimulation energy level, but also measure the amplitude of the peak of endocardial acceleration before (PEA1) and after (PEA2) the modification to the vagal stimulation energy level.

Similarly, steps 46, 48 and 50 of FIG. 3 are similar to steps 26, 28 and 30 of FIG. 2.

In step 46, if the test does not show an improvement in the filling time FT following an increase of the vagal stimulation energy level, the filing time is tested again against the target value S (step 52). If the filling time reaches the target value S, it is determined that the increase in the vagal stimulation energy did not improve the situation, and the vagal stimulation energy level is reduced or the stimulation is stopped (step 56), according to the same method as in step 32 of FIG. 2.

In step 52, if the test indicates that the target value S is reached, in step 54 the test of whether the contractility has increased is made by comparing the measurements of the peak amplitude before the increase of the vagal stimulation energy ("PEA1") and the peak amplitude after the increase of the vagal stimulation energy ("PEA2"). If the contractility is increased (PEA2>PEA1), the iterative process is completed, the vagal stimulation energy level is maintained at the current level, and the system waits for either the patient's state change (step 58), or the expiry of a predetermined timeout (steps 60, 62) to repeat the test with an adjustment to the vagal stimulation energy level. If, however, the test of step 54 reveals a decrease in contractility (PEA2<PEA1), the vagal stimulation energy level is restored to its previous level (step 50) such that the reduction of the stimulation energy level overcomes the deterioration of contractility.

One skilled in the art will appreciate that the present invention may be practiced by other elements and embodiments than the foregoing elements and embodiments discussed herein, which are provided for purposes of illustration but not of limitation.

What is claimed is:

1. An active implantable medical device for treating a patient, comprising:
    an electrode positioned to stimulate a vagus nerve of the patient;
    a generator electrically coupled to the electrode and configured to provide stimulation to the vagus nerve via the electrode;
    a sensor configured to measure a left ventricular filling time of the patient responsive to the stimulation; and
    a processor communicably coupled to the generator and the sensor, the processor configured to:
        adjust an energy level of the stimulation from a first level to a second level, varying the energy level of the stimulation during successive cardiac cycles;
        evaluate correlative changes in the left ventricular filling time by comparing the left ventricular filling time from the stimulation at the second level to the left ventricular filling time from the stimulation at the first level; and
        maintain the energy level of the stimulation at the second level based on the left ventricular filling time from the stimulation at the second level reaching a target value and being greater than the left ventricular filling time from the stimulation at the first level.

2. The medical device of claim 1, wherein the processor is configured to reduce the energy level of the stimulation based on the left ventricular filling time from the stimulation at the second level being equal to the left ventricular filling time from the stimulation at the first level.

3. The medical device of claim 1, wherein the sensor is configured to measure a peak endocardial acceleration of the patient responsive to the stimulation.

4. The medical device of claim 3, wherein the processor is configured to evaluate correlative changes in the peak endocardial acceleration by comparing the peak endocardial acceleration from the stimulation at the second level to the peak endocardial acceleration from the stimulation at the first level, wherein an increase in the peak endocardial acceleration indicates an increase in contractility.

5. The medical device of claim 4, wherein the processor is configured to maintain the energy level of the stimulation based further on the increase in the contractility.

6. The medical device of claim 1, wherein the processor is configured to adjust the energy level of the stimulation after a predetermined delay from a previous adjustment of the energy level.

7. The medical device of claim 1, wherein the sensor is further configured to detect a state change of the patient, wherein the processor is configured to adjust the energy level of the stimulation responsive to the state change of the patient.

8. The medical device of claim 7, wherein the state change of the patient includes at least one of a presence of arrhythmias, an absence of arrhythmias, and a transition between phases, the phases including a rest phase, an effort phase, and a sleep phase.

9. The medical device of claim 1, wherein the sensor includes at least one of a hemodynamic sensor, an endocardial acceleration sensor, an epicardial acceleration sensor, a myocardium wall motion sensor, an intracardiac pressure sensor, an intracardiac bioimpedance sensor, an optical oxygen saturation sensor, and an ultrasound sensor.

10. A method for adjusting a vagal stimulation of a medical device, comprising:
    providing stimulation to a vagus nerve of a patient;
    determining a left ventricular filling time of the patient responsive to the stimulation;
    adjusting the stimulation from a first scheme to a second scheme, wherein the stimulation is varied during different cardiac cycles;
    comparing the left ventricular filling time from the stimulation using the second scheme to the left ventricular filling time from the stimulation using the first scheme; and
    setting a stimulation scheme as the second scheme based on a determination that the left ventricular filling time from the stimulation using the second scheme reaches a target value and is greater than the left ventricular filling time from the stimulation using the first scheme.

11. The method of claim 10, further comprising measuring a cardiac response of the patient responsive to the stimulation to the vagus nerve, wherein the left ventricular filling time is determined based on the cardiac response of the patient.

12. The method of claim 10, further comprising measuring a peak endocardial acceleration of the patient responsive to the stimulation to the vagus nerve.

13. The method of claim 12, further comprising comparing the peak endocardial acceleration from the stimulation using the second scheme to the peak endocardial acceleration from the stimulation using the first scheme, wherein an increase in the peak endocardial acceleration indicates an increase in contractility.

14. The method of claim 13, wherein setting the stimulation scheme is based further on an indication that the contractility increases.

15. The method of claim 10, further comprising adjusting the stimulation scheme of the stimulation after a predetermined delay from a previous adjustment of the energy level.

16. The method of claim 10, further comprising adjusting the stimulation scheme of the stimulation responsive to a detection of a state change of the patient.

17. The method of claim 16, wherein the state change of the patient includes at least one of a presence of arrhythmias, an absence of arrhythmias, and a transition between phases, the phases including a rest phase, an effort phase, and a sleep phase.

18. A non-transitory computer readable medium storing a computer readable program for adjusting a vagal stimulation energy level of a medical device, comprising:
    computer readable instructions to acquire, from a sensor, a left ventricular filling time of a patient responsive to stimulation to a vagus nerve of the patient;
    computer readable instructions to adjust an energy level of the stimulation from a first level to a second level, wherein the energy level of the stimulation is varied for different cardiac cycles;
    computer readable instructions to compare the left ventricular filling time from the stimulation at the second level to the cardiac cycle parameter from the stimulation at the first level; and
    computer readable instructions to maintain the energy level of the stimulation at the second level based on the left ventricular filling time from the stimulation at the second level reaching a target value and being greater than the left ventricular filling time from the stimulation at the first level.

* * * * *